(12) United States Patent
Daugherty (10) Patent No.: US 10,000,931 B1
(45) Date of Patent: Jun. 19, 2018

(54) APPARATUS AND METHOD FOR MOSS REMEDIATION (71) Applicant: Daniel T. Daugherty, Lakebay, WA (US)

(72) Inventor: Daniel T. Daugherty, Lakebay, WA (US)

( * ) Notice: Subject to any disclaimer, the term of this patent is extended or adjusted under 35 U.S.C. 154(b) by 0 days. days.

(21) Appl. No.: 15/377,733

(22) Filed: Dec. 13, 2016

(51) Int. Cl.
*B65D 33/02* (2006.01)
*E04D 13/00* (2006.01)
*A01N 25/00* (2006.01)
*A01N 25/34* (2006.01)
*A01N 59/16* (2006.01)
*A01N 59/20* (2006.01)
*A01N 59/00* (2006.01)

(52) U.S. Cl.
CPC ........... *E04D 13/002* (2013.01); *A01N 25/00* (2013.01); *A01N 25/34* (2013.01); *A01N 59/00* (2013.01); *A01N 59/16* (2013.01); *A01N 59/20* (2013.01)

(58) Field of Classification Search
CPC ...... B65D 33/002; B65D 75/42; B65D 75/46; A01N 59/20; A01N 25/12; E04D 13/002
See application file for complete search history.

(56) References Cited

U.S. PATENT DOCUMENTS

| 927,132 | A | * | 7/1909 | Duenwald | E03D 9/032 4/231 |
|---|---|---|---|---|---|
| 2,329,429 | A | * | 9/1943 | Weaver | C02F 1/687 422/274 |
| 2,807,807 | A | * | 10/1957 | Harper | E03D 9/038 134/22.16 |
| 3,254,828 | A | * | 6/1966 | Lerner | B65B 43/123 206/820 |
| 3,479,130 | A | | 11/1969 | Rapaport | |
| 3,494,727 | A | | 2/1970 | Rapaport | |
| 3,566,832 | A | * | 3/1971 | Williams | E04D 13/002 118/506 |
| 3,613,309 | A | * | 10/1971 | Coburn | A01G 27/005 239/145 |
| 3,696,623 | A | * | 10/1972 | Heine | E02B 3/04 405/19 |
| 4,100,104 | A | | 7/1978 | Katzen et al. | |
| 4,112,409 | A | | 9/1978 | Jacquelin | |
| 4,276,732 | A | | 7/1981 | Nielsen | |
| 4,416,854 | A | * | 11/1983 | Nielsen | A01N 59/16 205/701 |
| 4,554,862 | A | | 11/1985 | Wolfert | |
| 4,616,055 | A | | 10/1986 | Mason | |
| 4,817,214 | A | * | 4/1989 | Stuessy | C02F 1/688 4/222 |
| 4,832,206 | A | * | 5/1989 | Cunningham | A47L 15/505 211/119.1 |

(Continued)

*Primary Examiner* — Brian E Glessner
*Assistant Examiner* — Daniel J Kenny
(74) *Attorney, Agent, or Firm* — George A. Leone; Citadel Patent Law (57) ABSTRACT

An apparatus for mold remediation on a building roof. A porous, stretchable tube includes two opposing folding end elements. Many mold remediation particles are contained within the tube. The porous, stretchable tube is made of a weather resistant material having multiple material openings so as to allow moisture to penetrate to the mold remediation particles while being sized smaller than the mold remediation particles so as to retain them in the tube.

14 Claims, 6 Drawing Sheets

(56) References Cited

U.S. PATENT DOCUMENTS

| | | | |
|---|---|---|---|
| 5,119,604 | A | 6/1992 | Peterson et al. |
| 5,216,864 | A | 6/1993 | Urgero |
| 5,253,616 | A | 10/1993 | Voss |
| 5,579,794 | A * | 12/1996 | Sporta .................... E02D 5/801 135/115 |
| 6,749,085 | B2 | 6/2004 | Garrant et al. |
| 7,329,069 | B2 * | 2/2008 | Slater ...................... E02B 3/108 383/32 |
| 7,354,596 | B1 | 4/2008 | Banovetz et al. |
| 7,788,870 | B1 | 9/2010 | Spencer |
| 8,333,639 | B2 | 12/2012 | Collister |
| 8,524,359 | B2 | 9/2013 | Tsunemori et al. |
| 8,656,562 | B2 | 2/2014 | Yang |
| 2003/0150170 | A1 | 8/2003 | Weber |
| 2006/0168899 | A1 * | 8/2006 | Buckenmaier, Jr. .. E04D 13/002 52/24 |
| 2010/0109318 | A1 | 5/2010 | Mulligan |

\* cited by examiner

APPARATUS AND METHOD FOR MOSS REMEDIATION

TECHNICAL FIELD

The present invention relates to methods and apparatus for moss remediation on buildings. More particularly, the invention relates to moss remediation system using a porous, stretchable tube containing zinc particles.

BACKGROUND

In many wet climates, particularly in the US Pacific Northwest, for example, moss, fungi, and algae cause roof discoloration which grows over time. Until now remedies have included installing zinc exposed strips which are affixed near the top of a roof ridge, for example. Other solutions have included roofing materials incorporating metallic elements such as in U.S. Pat. No. 3,494,727, issued Feb. 10, 1970.

U.S. Pat. No. 3,479,130, teaches mounting flat bimetallic strips horizontally along a rooftop to inhibit microbial or fungal growths which darken rooftops in semitropical and tropical climates. It is believed that the use of two metals, such as copper and lead, between which an electrolytic action results when rainwater contacts the metals. Such action dissolves ions of the metals into the water to create a solution which kills the microbes and fungus. To obtain adequate coverage of a rooftop multiple strips are used, such strips being vertically spaced four to ten shingles apart.

Unfortunately, these prior attempts at eliminating roof discoloration due to biological growth have several drawbacks. For example, zinc strips have limited periods of effectiveness since they lose effectiveness from exposure to the sun in the summer and tend to warp away from contact with the composition roof becoming "U-shaped". Installation for zinc strips or bimetallic combination strips is labor-intensive because it typically requires affixing roofing nails spaced approximately every two feet. Microbe resistant roofing materials do not offer much of an advantage since they cannot be easily retrofitted to an existing roof without replacing substantially the entire roof.

In a striking improvement over conventionally available moss remediation devices, the present invention for the first time provides a hose-like mold remediation stretch strip that is easily secured to any existing roof. Further, for many applications, the moss remediation apparatus disclosed herein can be rotated for maximum mold remediation exposure when needed. An added advantage of the instant invention is that roofing nails will not be required as used in installing zinc strips. In a further advantage over rectangular zinc strips, the exposed volume of a spherical particle surface area is roughly at least double the exposed volume of a similar surface area of a rectangular zinc strip.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

Disclosed herein is an apparatus for mold remediation on a building roof. At least one porous, stretchable tube includes two opposing folding end elements. A plurality of mold remediation particles is contained within the at least one tube. The porous, stretchable tube comprises a weather resistant material having multiple material openings so as to allow moisture to penetrate to the mold remediation particles while being sized smaller than the mold remediation particles so as to retain them in the at least one tube.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

In the drawings, identical reference numbers call out similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not necessarily intended to convey any information regarding the actual shape of the particular elements, and have been solely selected for ease of recognition in the drawings.

DETAILED DESCRIPTION OF THE PREFERRED EMBODIMENTS

The following disclosure describes an apparatus for moss remediation. Several features of methods and systems in accordance with example embodiments are set forth and described in the figures. It will be appreciated that methods and systems in accordance with other example embodiments can include additional procedures or features different than those shown in the figures. Example embodiments are described herein with respect to a porous flexible tube containing zinc particles for mounting on a roof. However, it will be understood that these examples are for the purpose of illustrating the principles, and that the invention is not so limited.

DEFINITIONS

Generally, as used herein, the following terms have the following meanings, unless the use in context dictates otherwise:

The use of the word "a" or "an" when used in conjunction with the term "comprising" in the claims or the specification means one or more than one, unless the context dictates otherwise. The term "about" means the stated value plus or minus the margin of error of measurement or plus or minus 10% if no method of measurement is indicated. The use of the term "or" in the claims is used to mean "and/or" unless explicitly indicated to refer to alternatives only or if the alternatives are mutually exclusive. The terms "comprise", "have", "include" and "contain" (and their variants) are open-ended linking verbs and allow the addition of other elements when used in a claim.

Reference throughout this specification to "one example" or "an example embodiment," "one embodiment," "an embodiment" or combinations and/or variations of these terms means that a feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the features, structures, or characteristics may be combined in any suitable manner in one or more embodiments.

As used herein, "plurality" or "set" are understood to mean more than one. For example, a plurality or set refer to at least two, three, four, five, ten, 25, 50, 75, 100, 1,000, 10,000 or more.

DETAILED DESCRIPTION OF THE FIGURES

Figure 1:
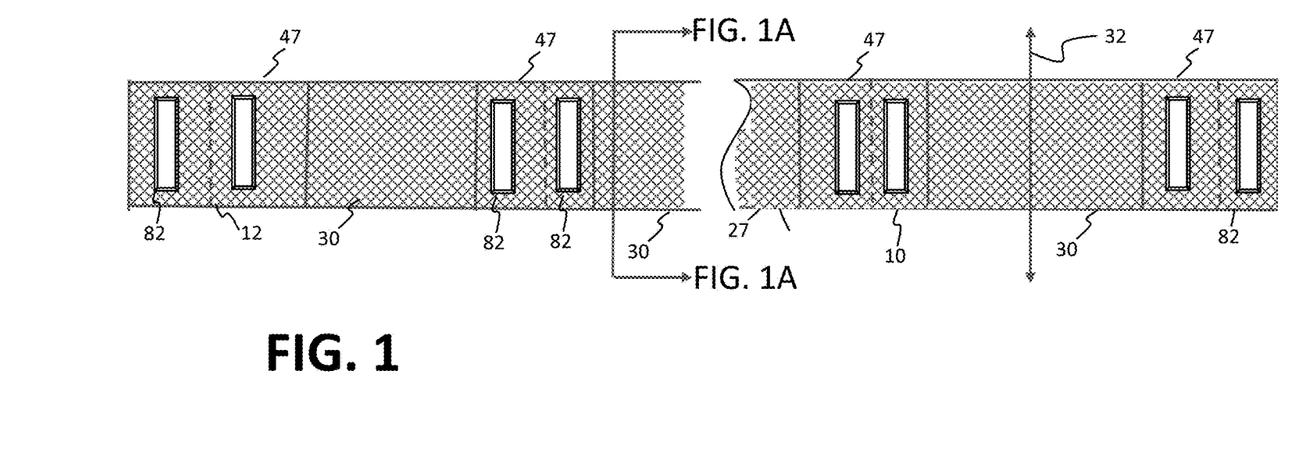
FIG. 1 schematically shows a porous, stretchable mold remediation filled tube.

Referring now to FIG. 1, a porous, stretchable mold remediation particle-filled tube is schematically shown. A porous, stretchable mold remediation particle-filled tube 10 may advantageously include a series of uniformly spaced flat sealed sections 47 and mold remediation particle-filled sections 30. Cutting lines 12 for sectioning the tube 10 into various lengths generally bisect the uniformly spaced flat sections 47. A plurality of pairs of slots 82 are located in each sealed flat section 47 to allow securing a tube to another tube or to a roof section as explained in detail below.

In one example, the tube 10 may be made from porous material such as porous fabric, nylon, sun resistant fabrics, plastic mesh, plastic netting and combinations thereof or the like. As indicated by double headed arrow 32, the tube 10 is made of a stretchable fabric. The fabric may comprise a weave or mesh with openings sized to allow rain or other precipitation to penetrate the mold remediation particles. When in use, the tube 10 may be stretched in the vertical and horizontal directions. In one example the tube is packed with zinc particles at a packing density that allow stretching of the material up to 2.5 inches in width. The tubes may also come in lengths of about 50 feet up to about 60 feet, which is in turns stretchable up to about 55 feet and about 65 feet respectively. Multiple tubes may be joined together for longer roofs. The tubes may also be sectioned along the cutting lines 12 to adjust for length. Cutting lines 12 may be perforations, marked lines, simple depressions or the like.

Figure 1A:
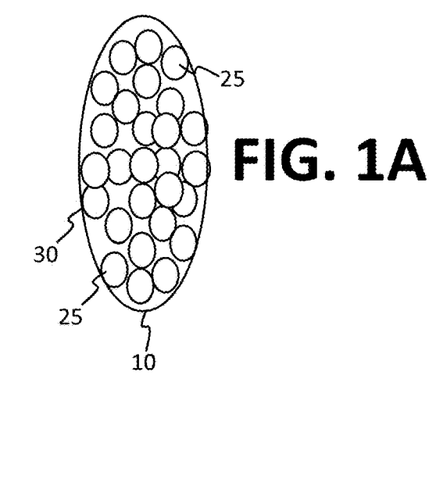
FIG. 1A schematically shows a cross-section of the porous, flexible mold remediation particle-filled tube of FIG. 1.

Referring now to FIG. 1A, a cross-section of the porous, flexible particle-filled tube of FIG. 1 is schematically shown. Filling each filled section 30 of the tube 10 are a plurality of mold remediation particles 25 which may be advantageously made from various compounds including copper, nickel, zinc oxide, zinc chloride, zinc sulfate, and zinc carbonate. Combinations of compounds of copper and iron and lead and zinc have been found to be particularly beneficial for mold remediation in some instances. In some examples, the tube and/or particles may be treated with bleach or borate compound to promote initial moss elimination. In some examples, the mold remediation particles may comprise marble sized balls having a cross-sectional diameter of about ⅜ inches and the openings 27 in the fabric of the tube 10 may be about ¼ inch and/or sized to retain the particles when the fabric is fully stretched. Other sizes of openings may be used with correspondingly larger or smaller zinc particles. Mold remediation particles must be, of course, larger than the openings. The particles may be solid or hollow.

Figure 2:
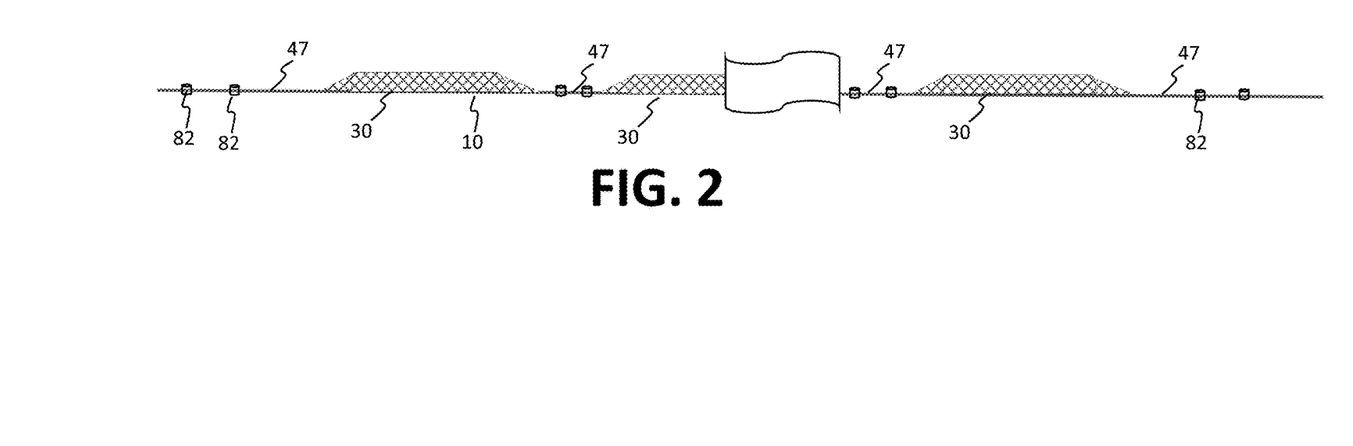
FIG. 2 schematically shows an elevated side view of the porous, flexible mold remediation particle-filled tube of FIG. 1.

Referring now to FIG. 2, an elevated side view of the porous, flexible particle-filled tube of FIG. 1 is schematically shown. In one example, the sealed flat sections 47 may have a length of about 1 inch uniformly spaced between sections of particle filled portions 30. The particle filled portions 30 may have a length, for example, of about 2 feet.

Figure 3:
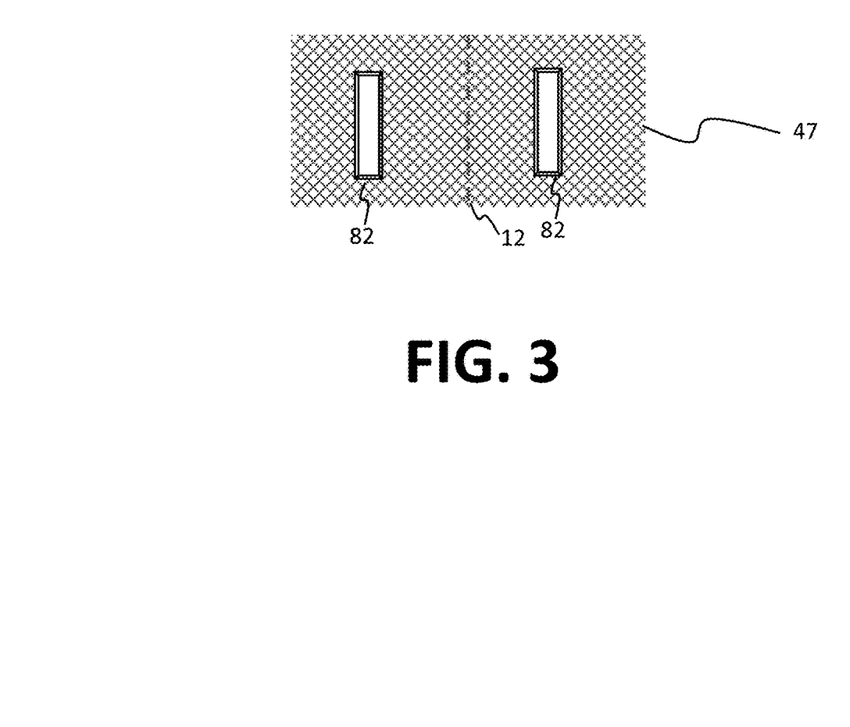
FIG. 3 schematically shows a more detailed top view of a sealed flat section with slots for combining tubes.

Referring now to FIG. 3, a more detailed top view of a sealed flat section with slots for combining tubes is schematically shown. The sealed flat section 47 may be separated along cutting line 12 for shortening or otherwise sectioning a tube 10. The slots 82 are sized to accept joining strips as shown in more detail below. The sealed flat section 47 may be heat sealed, compressed, or otherwise treated to seal the particles into the adjacent filled portion. In some embodiments, a hardware clip, such as a spring-loaded clip, spring biased jaws, ratchet mechanisms, a plastic clip, or the like may be employed to compress the sealed flat section 47.

Figures 4, 5:
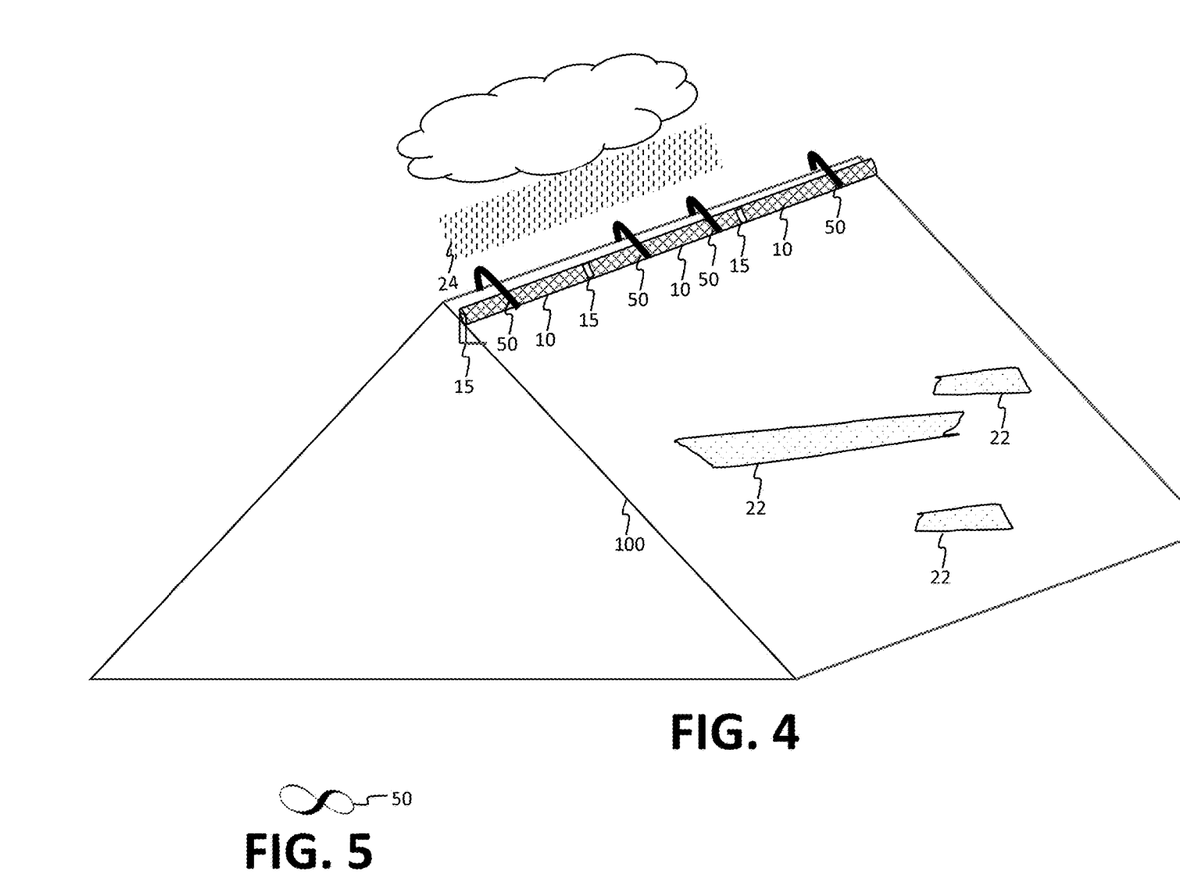
FIG. 4 schematically shows a porous, stretchable, mold remediation particle-filled tube as assembled proximate the ridge of a roof.
FIG. 5 schematically shows a holding fixture configured in a FIG. 8 loop to hold parallel tubes.

Referring now to FIG. 4, a porous, stretchable, particle-filled tube as assembled proximate the ridge of a roof is schematically shown. A porous, flexible particle-filled tube 10 is mounted on a roof 100 using a plurality of holding fixtures 50. In this example, joining strips 15 join three mold remediation filled tubes 10 in a linear fashion. An end joining strip 15 is folded over and fastened under an eave of the roof 100, as shown below in more detail with reference to FIG. 9. Discolored or moldy areas of the roof are represented by patches 22. After installation, precipitation 24 causes ionization of the mold remediation particles which flows downward into the patches 22 and reacts to dissolve the mold or other biological factor.

Referring now to FIG. 5, an example of a holding fixture configured to hold parallel tubes is schematically shown. The holding fixture 50 comprises, for example, a cable or plastic tie strip configured as a "FIG. 8" loop. When in use, a separate tube is inserted into each loop and the center of the loop rests on the roof ridge, thereby holding a pair of tubes in a parallel arrangement on either side of the roof 100. Other holding fixtures may be employed as will be evident to those skilled in the art having the benefit of this disclosure. These may include, for example, straps, clips, tubular collars and the like.

Figure 6:
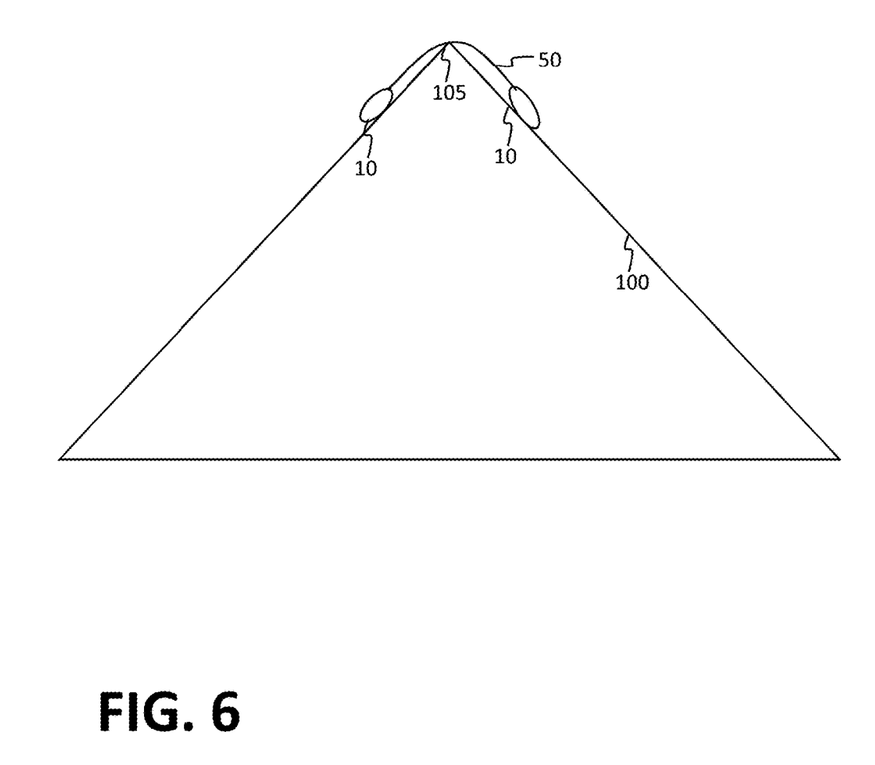
FIG. 6 schematically shows a side view of a peaked roof where a ridge bracket and a pair of flexible mold remediation particle-filled tubes have been installed.

Referring now to FIG. 6, a partial side view of a ridge bracket with a tube installed is schematically shown. A tube 10 is shown inserted into a holding fixture 50 over a roof ridge 105. When in use, about four holding fixtures will support a pair of tubes each having a typical length of about 50-60 feet.

Figure 7:
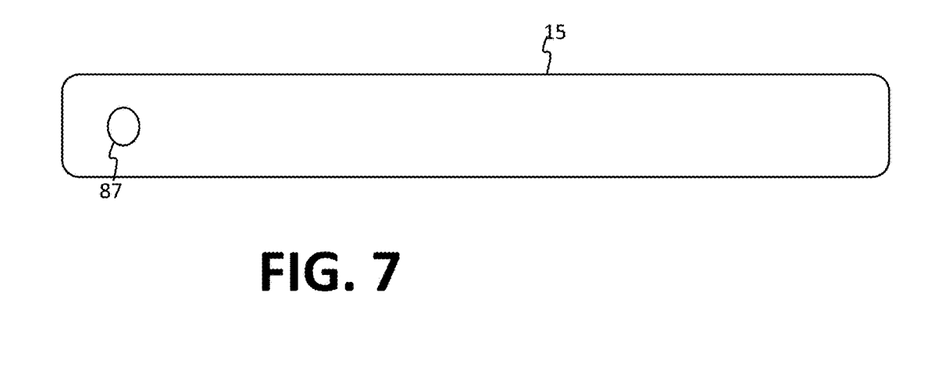
FIG. 7 schematically shows a securing strip as used to secure the porous, stretchable, mold remediation particle-filled tube.

Referring now to FIG. 7, a securing strip as used to secure the porous, stretchable, mold remediation particle-filled tube is schematically shown. The securing strip 15, if used as an end piece, may include at least one nail hole 87 and is sufficiently pliable to bend around a roof edge, such as an eave for securing the tube 10. Each end of a tube, or series of tubes will terminate in a securing strip 15. Similarly, a strip with or without a nail hole may be used to join together a series of tubes for the purpose of covering a longer roof or making a customized length of tubing by bending the strip around and through a pair of adjoining tube end slots 82, for example. The strip 15, may comprise, for example, any sturdy flexible material like pot metal, copper, zinc, or even plastic straps or certain fabrics if sufficiently strong and weather resistant, and the like.

Figure 8:
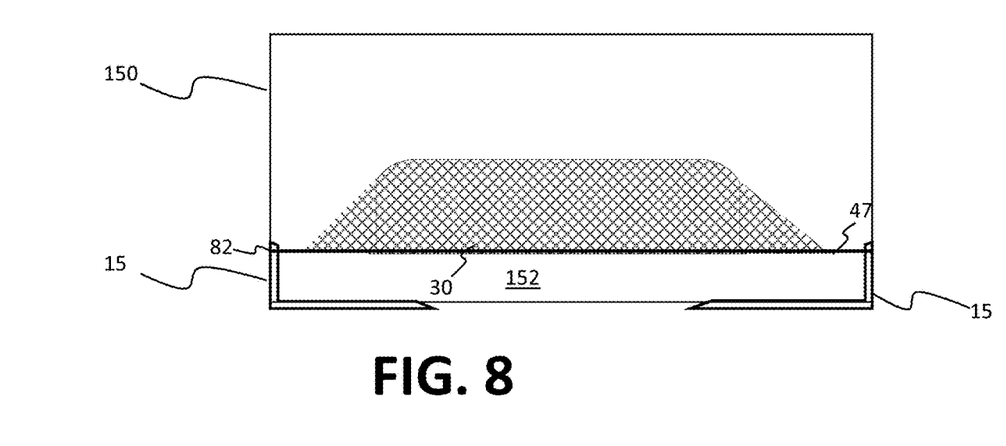
FIG. 8 schematically shows a section of filled tubing affixed proximate a roof vent.

Referring now to FIG. 8, a section of filled tubing affixed proximate a roof vent is schematically shown. On a typical roof, structures, such as roof vents 150, protrude above the roof line and will tend to block the flow of mold remediation mixtures from above their position. In such cases, it is advantageous to locate a short section of a tube comprising one particle filled section 30 bracketed by a pair of sealed sections 47 on the backside of the event 150 or other structure. A pair of securing strips 15 may be attached to the sealed sections as by folding a first end of each strip through the slots 82 and the second end under a shingle 152, for example.

Figure 9:
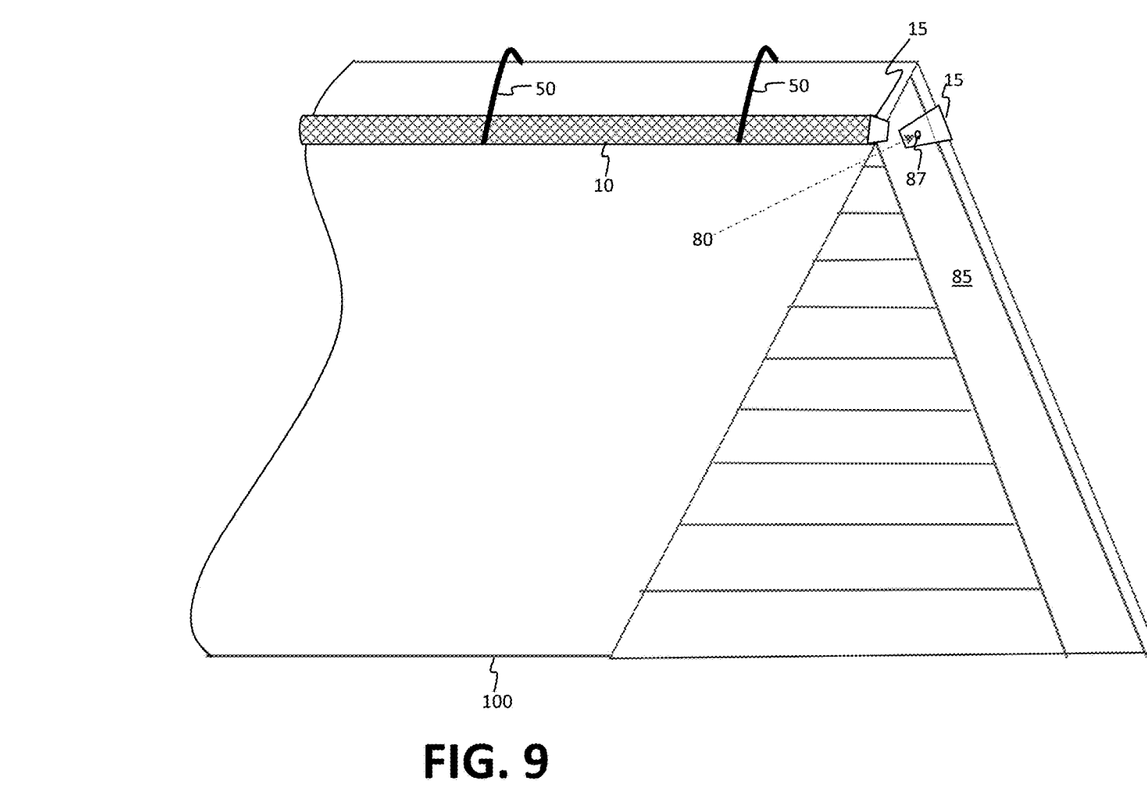
FIG. 9 schematically shows an installation diagram for installing a porous, flexible, mold remediation particle-filled tube onto a peaked roof.

Referring now to FIG. 9, a more detailed perspective view of an end bracket affixed under a roof eave it is schematically shown. Once tubes 10 have been mounted on a roof 100, using, for example, holding fixtures 50, securing strips 15 at each end of the tube 10 or plurality of adjoined tubes 10 are folded over and fastened under eave 85. A hole 87 is provided for inserting a fastener, such as a nail, screw or the like as indicated by broken line 80.

Having described the configuration of the example embodiments, it will now be useful to the understanding of the invention to describe how the various components are manufactured. The devices can be constructed from any material having properties that make the material satisfactory for use on a roof with constant exposure to weather. In some instances, it may be desirable to rotate the mold remediation filled tubes on a periodic basis, such as annually, in order to enhance the mold remediation effects. Zinc pellets, particles, buttons or balls may be purchased or fabricated. For example, zinc button sized discs may be fabricated by punching zinc sheets with a ¼ inch punch. Further, the material may be selected in various colors to match roof materials for aesthetic purposes. Matching colors will blend in more easily with a roof and may be more pleasing to the eye. In one alternate embodiment, a perforated tube such as a flexible garden hose or the like may be used in place of nylon or other reason weather resistant materials.

The invention has been described herein in considerable detail to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

What is claimed is:

1. An apparatus for mold remediation on a building roof comprising:
   at least one porous, stretchable tube having two opposing folding end elements, wherein the stretchable tube further comprises a series of uniformly spaced flat sealed sections distributed between a series of mold remediation particle-filled sections with cutting lines for sectioning the tube into various lengths where the cutting lines generally bisect the uniformly spaced flat sections and a plurality of pairs of slots are located in each sealed flat section to allow securing a tube to another tube or to a roof section;
   a plurality of mold remediation particles contained within the at least one tube; and
   wherein the porous, stretchable tube comprises a weather resistant material having multiple material openings so as to allow moisture to penetrate to the mold remediation particles while being sized smaller than the mold remediation particles so as to retain them in the at least one tube.

2. The apparatus of claim 1 wherein the at least one tube comprises a pair of parallel tubes, and further including a plurality of holding fixtures connecting the parallel tubes.

3. The apparatus of claim 1 wherein the at least one tube comprises a linear tube measuring up to 60 feet, which is stretchable up to 65 feet.

4. The apparatus of claim 1 wherein the at least one tube comprises material selected from the group consisting of porous fabric, nylon, sun resistant fabrics, plastic mesh, plastic netting and combinations thereof.

5. The apparatus of claim 1 wherein the at least one tube comprises a stretchable fabric that can stretch vertically and horizontally when packed with mold remediation particles.

6. The apparatus of claim 1 wherein the mold remediation particles are selected from the group consisting of nickel, copper, copper and iron compounds, lead and zinc compounds, zinc oxide, zinc chloride, zinc sulfate, zinc carbonate, bleach treated particles and combinations thereof.

7. The apparatus of claim 1 wherein the mold remediation particles comprise spheres having a cross-sectional diameter of at least ⅜ inches.

8. A mold remediation installation system for a building roof comprising:

a pair of porous, stretchable tubes, each tube having two opposing folding end elements, the pair of tubes connected in parallel with a plurality of holding fixtures for linearly mounting adjacent a roof ridge, wherein each tube further comprises a series of uniformly spaced flat sealed sections distributed between a series of mold remediation particle-filled sections, wherein the two opposing folding end elements are adapted to be secured to a terminal portion of the building roof;

a plurality of mold remediation particles contained in each tube; and wherein each tube comprises a weather resistant material having multiple material openings so as to allow moisture to penetrate to the mold remediation particles while being sized smaller than the mold remediation particles so as to retain them in the tube.

9. The system of claim 8 further comprising cutting lines for sectioning each tube into various lengths where the cutting lines generally bisect the uniformly spaced flat sections and a plurality of pairs of slots are located in each sealed flat section to allow securing a tube to another tube or to a roof section.

10. The system of claim 8 wherein each tube comprises a linear tube measuring up to 60 feet, which is stretchable up to 65 feet.

11. The system of claim 8 wherein the at least one tube comprises material selected from the group consisting of porous fabric, porous fabric, nylon, sun resistant fabrics, plastic mesh, plastic netting and combinations thereof.

12. The system of claim 8 wherein each tube comprises a stretchable fabric that can stretch vertically and horizontally when packed with mold remediation particles.

13. The system of claim 8 wherein the mold remediation particles are selected from the group consisting of nickel, copper, copper and iron compounds, lead and zinc compounds, zinc oxide, zinc chloride, zinc sulfate, zinc carbonate, bleach treated particles and combinations thereof.

14. The system of claim 8 wherein the mold remediation particles comprise spheres having a cross-sectional diameter of at least 3/8 inches.

* * * * *